United States Patent [19]

Eierdanz et al.

[11] Patent Number: 5,278,327
[45] Date of Patent: Jan. 11, 1994

[54] FATTY OIL EX HELIANTHUS ANNUUS FOR THE PRODUCTION OF DIPERAZELAIC ACID

[75] Inventors: Horst Eierdanz, Hilden; Paul Schulz, Wuppertal; Beatrix Kottwitz, Duesseldorf, all of Fed. Rep. of Germany

[73] Assignee: Henkel Kommanditgesellschaft auf Aktien, Duesseldorf, Fed. Rep. of Germany

[21] Appl. No.: 190,862

[22] Filed: May 6, 1988

[30] Foreign Application Priority Data

May 8, 1987 [DE] Fed. Rep. of Germany ....... 3715464

[51] Int. Cl.$^5$ .............................................. C07C 51/16
[52] U.S. Cl. ..................................... 554/150; 562/524
[58] Field of Search ............. 260/502 R, 406; 562/524; 554/150

[56] References Cited

U.S. PATENT DOCUMENTS

| | | | |
|---|---|---|---|
| 2,450,858 | 10/1948 | Fitzpatrick et al. | 260/406 |
| 2,813,113 | 11/1957 | Goebel et al. | 260/406 |
| 2,877,266 | 3/1959 | Korach | 260/502 R |
| 4,147,720 | 4/1979 | Berkowitz | 260/502 R |
| 4,244,884 | 1/1981 | Hutchins et al. | 260/502 R |
| 4,627,192 | 12/1986 | Fick | 47/58 |

FOREIGN PATENT DOCUMENTS 0127782 12/1984 European Pat. Off. .

OTHER PUBLICATIONS

D. Swern et al., J. Am., Chem. Soc., 79, 1957, pp. 1929 et seq.

Primary Examiner—José G. Dees
Assistant Examiner—Joseph M. Conrad, III
Attorney, Agent, or Firm—Ernest G. Szoke; Wayne C. Jaeschke; Henry E. Millson, Jr.

[57] ABSTRACT

The use of a fatty oil ex *Helianthus annuus* containing 78 to 92% by weight oleic acid and 2 to 10% by weight linoleic acid for the production of diperazelaic acid, with elimination of enrichment steps with respect to the oleic acid content, by fat splitting, distillation, oxidative ozonolysis of the fatty acid mixture obtained, and reaction of the azelaic acid thus obtained with hydrogen peroxide to form diperazelaic acid. The resulting diperazelaic acid has improved stability in storage and is obtained in high yields and in highly pure form.

14 Claims, No Drawings

FATTY OIL EX HELIANTHUS ANNUUS FOR THE PRODUCTION OF DIPERAZELAIC ACID

BACKGROUND OF THE INVENTION

1. Field of the Invention

This invention relates to the production of diperazelaic acid from a fatty oil obtained from *Helianthus annuus*.

2. Statement of Related Art

The production of azelaic acid by oxidative ozonolysis of technical oleic acid is known from U.S. Pat. No. 2,450,858 and from U.S. Pat. No. 2,813,113. It is also known that diperazelaic acid can be produced by reaction of technical oleic acid with hydrogen peroxide in the presence of sulfuric acid, cf. D. Swern et al., J. Am, Chem. Soc., 79, 1929 et seq (1957); M. Dankowski, EP-A 127,782.

In the production of azelaic acid from technical oleic acid, it has been found that the presence of polyunsaturated fatty acids in the technical oleic acids used has an unfavorable effect due to the increased formation of secondary products. In addition, the technical oleic acid normally used is obtained by enrichment (solvent or hydrophilization processes) and purification of the oleic acid present in split tallow fatty acid. However, fundamental limits are imposed on the enrichment processes for recovering the oleic acid. Technically, therefore, 65 to 70% oleic acid is used in the production of azelaic acid.

DESCRIPTION OF THE INVENTION

Other than in the operating examples, or where otherwise indicated, all numbers expressing quantities of ingredients or reaction conditions used herein are to be understood as modified in all instances by the term "about".

It has now been found that a highly pure azelaic acid can be obtained in high yields from a fatty oil of a *Helianthus annuus* species described, for example, in U.S. Pat. No. 4,627,192, which is expressly incorporated herein by reference. The diperazelaic acid produced from the azelaic acid thus obtained surprisingly shows a higher stability than that produced in accordance with the prior art using a split tallow fatty acid enriched and purified by elaborate processes although, at 7 to 10%, the fatty acid ex *Helianthus annuus* contains as high a proportion of diunsaturated fatty acids as the split tallow fatty acid.

More particularly, this invention relates to the use of a fatty oil ex *Helianthus annuus* containing 78 to 92% by weight oleic acid and 2 to 10% by weight linoleic acid, based on total fatty acids present, balance (to 100% by weight) optionally palmitic acid and stearic acid and up to 1% by weight fatty acids from the group: myristic, palmitoleic, linolenic, arachic, eicosenoic, and erucic acid, with elimination of enrichment steps with respect to the oleic acid content, for the production of diperazelaic acid by
  a) fat splitting,
  b) distillation,
  c) oxidative ozonolysis of the fatty acid mixture obtained to form azelaic acid, and
  d) reaction of the azelaic acid thus obtained with hydrogen peroxide to form diperazelaic acid.

By "distillation" is meant simple overhead distillation without fractionation of the distillate.

The fatty oils ex *Helianthus annuus* to be used in accordance with the invention are natural products, so that they are subjected to certain variations with respect to the compositions of their constituents. They can have the following compositions with respect to their principal components (percentages by weight are based on total weight of fatty acids present therein):

| | |
|---|---|
| oleic acid | 78 to 92% by weight |
| linoleic acid | 2 to 10% by weight |
| palmitic acid | 2 to 5% by weight |
| stearic acid | 2 to 7% by weight |

The species and lines of *Helianthus annuus* from which the fatty oils used in the present invention are preferably obtained include SIGCO 41A, SIGCO 41B, SIGCO 4117B, SIGCO 416R, SIGCO 853R, SIGCO 273 W, and sunflower lines based on the foregoing.

It has been found that diperazelaic acid obtained using the fatty oils according to the invention is considerably easier to purify; the pure azelaic acid obtained as an intermediate stage can also be purified by simple crystallization, for example from apolar solvents or from water. Also, the consumption of ozone in the ozonolysis of oleic acid obtained from the fatty oil having the above-indicated composition to be used in accordance with the invention is distinctly reduced.

In the process of the invention, step a) is carried out as follows: the fatty oil is reacted with water at a temperature in the range of 150° to 250° C., preferably 185° to 215° C. under a pressure of from 15 to 50 bar, preferably 20 to 35 bar. After 5 or 6 hours the glycerol/water phase is separated and the above procedure preferably repeated twice to improve the yield. After the last separation of the glycerol/water phase, the resulting fatty acid mixture is distilled under reduced pressure (step b)). The distilled fatty acid mixture is then subjected to oxidative ozonolysis (step c)). Step c) is carried out by reacting the distilled fatty acid mixture with an ozone/air mixture in the presence of water at a temperature in the range of from 20° to 40° C., preferably around 30° C. Following the reaction the reaction mixture is allowed to separate into two phases, and the organic phase is separated from the aqueous phase. Further oxidation of the organic phase is desireable, e.g. by the following: air oxidation at 60° to 100° C., followed by treatment with hydrogen peroxide at 80° to 95° C., and finally heating at 120°-140° C. to thermally degrade the peroxide. The azelaic acid thus obtained is then reacted with hydrogen peroxide according to the process disclosed in J. Am. Chem. Soc. 79, 1931 (1957), which is carried out by first contacting the fatty azelaic acid with concentrated sulfuric acid, followed by the addition of hydrogen peroxide, preferably in excess, e.g. 100% excess, at a temperature maintained at 20° to 25° C. and the reaction mixture stirred for a period of e.g. from 3 to 5 hours. The diperazelaic acid is then isolated from the reaction mixture, e.g. by precipitation from an aqueous ammonium sulfate solution.

The invention is illustrated by not limited by the following Example.

EXAMPLE

5 Kg of sunflower oil obtained from a *Helianthus annuus* species covered by U.S. Pat. No. 4,627,192 was split in the presence of 0.6 kg water at 200° C./20-35 bar in 5-6 hours. After separation of the glycerol/water phase the above fat splitting step was repeated twice. After final removal of water and glycerol the fatty acid mixture was distilled at 160°-190° C./0.2-0.3 bar.

The fatty acid mixture had the following composition as determined by gas chromatography:

| | |
|---|---|
| myristic acid | 0.1% by weight |
| palmitic acid | 3.1% by weight |
| stearic acid | 2.0% by weight |
| oleic acid | 86.2% by weight |
| linoleic acid | 7.8% by weight |
| linolenic acid | 0.2% by weight |
| arachic acid | 0.2% by weight |
| eicosenoic acid | 0.2% by weight |

4570 g/h of a 20% solution of the above fatty acid mixture in pelargonic acid, 915 g/h water, which was intensively homogenized with the above organic phase in a dynamic mixer before entry into the reaction column, and 140 g/h ozone in the form of a 3% ozone/air mixture were introduced downwards in co-current into a Metallapack-filled fine steel column. The reaction temperature was stabilized at around 30° C. by evaporation of most of the water in the carrier air stream. After phase separation, the reaction product gave an organic layer which was subsequently worked up by oxidation in three steps in a glass or enamel reactor:

1. by oxidation with air at 80° C. (70 l air/h/kg reaction mixture), the oxidation air being saturated with steam at 60° C. before introduction into the reactor; the oxidation with air lasted about 1.5 hours.
2. Re-oxidation with hydrogen peroxide (28.5 g 70% $H_2O_2$ solution/kg reaction mixture) at 90° C.; the reoxidation lasted about 2 hours.
3. thermal peroxide degradation at 130° C. (approx. 1 hour).

The fully reacted mixture (peroxide value <20) was first separated from the pelargonic acid used as solvent and formed by splitting of oleic acid in a thin-layer evaporator (operating pressure 1 mbar, heat carrier temperature 160° C.). The residual melt (approx. 80% azelaic acid) was dissolved hot (approx. 95° C., ratio 1:1) in a crystallization medium (toluene or water) and cooled with defined stirring. The dried crystallizate (93 to 95% azelaic acid) corresponded to a yield of 85 to 87%, based on the oleic acid used. It was then directly used, i.e. without additional purification, for the production of diperazelaic acid.

The diperazelaic acid was produced in accordance with the publications cited above, J. Am. Chem. Soc. 79, 1929 et seq (1957); M. Dankowski, EP 127 762. More particularly, 100 g (0.53 mole) of azelaic acid was dissolved in 300 g. of 95% sulfuric acid in an open reaction vessel. With good stirring 105 g. (2 moles) of 65% hydrogen peroxide was added dropwise over a 5-10 minute period while maintaining the internal temperature at 20°-25° by an ice-water bath. Stirring was continued for an additional 8 hr. Several volumes of a half-saturated aqueous solution of ammonium sulfate (35 g./100 g. $H_2O$) were added at 0° and the precipitate of diperazelaic acid was filtered off. The product was washed on the funnel with the cold ammonium sulfate solution until the filtrate was free of sulfuric acid (several washes). The crude product was dried under vacuum at room temperature. Recrystallization from ethanol-water (1:5) yielded an analytically pure product.

The diperazelaic acid thus obtained was used as an effective bleach at low washing temperatures (30° to 60° C.). It showed improved stability in storage at 25° C. both in pure form and desensitized with sodium sulfate, as can be seen from the following Tables. Diperazelaic acid desensitized with sodium sulfate was obtained by dissolving 2 g pure diperazelaic acid in 50 ml warm dichloro methane. Then 4 g sodium sulfate, water-free were added. Dichloro methane was evaporated in vacuo at 40° C. The residue was homogenized by intensive mixing.

TABLE 1

Stability in storage of a diperoxyazelaic acid obtained in accordance with the invention.

| Days | Pure substance | 30% in $Na_2SO_4$ |
|---|---|---|
| | % decomposition | |
| 10 | stable | stable |
| 27 | 2% | 2% |
| 46 | 5% | 3% |

TABLE 2

Stability in storage of a diperoxyazelaic acid prepared from split tallow fatty acid

| Days | Pure substance | 30% in $Na_2SO_4$ |
|---|---|---|
| | % decomposition | |
| 12 | only storable for | 4% |
| 33 | prolonged periods | 4-8% |
| 50 | at +4° C. | 6-8% |

The yields of azelaic acid obtained with split tallow fatty acid and in accordance with the invention and the purities are shown in Table 3.

TABLE 3

| Azelaic acid yields (based on fatty acid used) and purities | | |
|---|---|---|
| | Starting Material | |
| | Split tallow fatty acid | Example fatty acid |
| Yield | 82.4% | 85.5% |
| Azelaic acid content of end product* | approx. 83% | approx. 95% |

*simple recrystallization from toluene

The consumption of ozone where tallow fatty acid was used in accordance with the prior art and the ozone consumption where the material according to the invention was used are compared in Table 4.

TABLE 4

| Ozone consumption using different olefins | | |
|---|---|---|
| | Starting Material | |
| | Split tallow fatty acid** | Example** |
| Ozone consumption (kg ozone per kg azelaic acid) | 0.493 | 0.323 |

**azelaic acid yields, see Table 3, ozone excess approx. 5% in either case

We claim:
1. A process for the preparation of diperazelaic acid comprising the steps of:
(A) reacting a fatty oil obtained from the seeds of *Helianthus annuus* and which contains from about 78 to about 92% by weight, based on the total weight of fatty acids present therein, of oleic acid, with water at a temperature in the range of from about 150° to about 250° C. to form a fatty acid phase and a glycerol/water phase, and separating the glycerol/water phase from the fatty acid phase,
(B) distilling the fatty acid phase,
(C) reacting the distilled fatty acid with an ozone/air mixture in the presence of water at a temperature in the range of from about 20° to about 40° C., to form azelaic acid, and (D) contacting the azelaic acid with concentrated sulfuric acid and hydrogen peroxide to form diperazelaic acid.

2. The process of claim 1 wherein in step (A) the fatty oil is obtained from at least one of the following lines of *Helianthus annuus:*

SIGCO 41A, SIGCO 41B, SIGCO 4117B, SIGCO 416R, SIGCO 853R, SIGCO 273 W, and sunflower lines based on the foregoing.

3. The process of claim 1 wherein in step (A) the temperature is in the range of from about 185° to about 215° C.

4. The process of claim 1 wherein in step (A) a pressure of from about 15 to about 50 bar is employed.

5. The process of claim 3 wherein in step (A) a pressure of from about 20 to about 35 bar is employed.

6. The process of claim 1 wherein step (A) is carried out three times prior to carrying out step (B).

7. The process of claim 1 wherein in step (C) additional oxidation procedures are carried out.

8. The process of claim 6 wherein in step (C) additional oxidation procedures are carried out.

9. The process of claim 1 wherein in step (D) excess hydrogen peroxide is present.

10. A process for the preparation of diperazelaic acid comprising the steps of (A) reacting a fatty oil obtained from the seeds of *Helianthus annuus* and which contains from about 78 to about 92% by weight, based on the total weight of fatty acids present therein, of oleic acid, without prior enrichment of the oleic acid content, with water at a temperature in the range of from about 185° to about 215° C., and under a pressure of from about 20 to about 35 bar to form a fatty acid phase and a glycerol/water phase, and separating the glycerol/water phase from the fatty acid phase, (B) distilling the fatty acid phase under reduced pressure, (C) reacting the distilled fatty acid with an ozone/air mixture in the presence of water at a temperature in the range of from about 20° to about 40° C., to form a reaction mixture which separates into an aqueous phase and an organic phase, (D) separating the organic phase from the aqueous phase, (E) air oxidizing the organic phase at a temperature of from about 60° C. to about 100° C., (F) treating the organic phase with hydrogen peroxide at a temperature of from about 80° C. to about 95° C., (G) heating the organic phase to a temperature of from about 120° to about 140° C. to thermally degrade the hydrogen peroxide, (H) contacting the organic phase with concentrated sulfuric acid followed by hydrogen peroxide at a temperature in the range of from about 20° to about 25° C. to form a reaction mixture containing diperazelaic acid, and (I) isolating the diperazelaic acid from the reaction mixture.

11. The process of claim 10 wherein the reaction of the fatty oil with water in step (A) is carried out at least three times.

12. The process of claim 10 wherein step (C) is carried out at a temperature of about 30° C.

13. The process of claim 10 wherein the hydrogen peroxide used in step (F) is used in excess.

14. The process of claim 10 wherein in step (A) the fatty oil is obtained from at least one of the following lines of *Helianthus annuus:*

SIGCO 41A, SIGCO 41B, SIGCO 4117B, SIGCO 416R, SIGCO 853R, SIGCO 273 W, and sunflower lines based on the foregoing.

* * * * *